US010010080B2

(12) United States Patent
Neigel

(10) Patent No.: US 10,010,080 B2
(45) Date of Patent: Jul. 3, 2018

(54) PROCESS FOR THE PRODUCTION OF PARTIALLY POLYMERIZED ANTIMICROBIAL SILANOL QUATERNARY AMMONIUM COMPOUNDS

(71) Applicant: Dennis Victor Neigel, Salisbury, NC (US)

(72) Inventor: Dennis Victor Neigel, Salisbury, NC (US)

(73) Assignee: Indusco, Ltd., Greensboro, NC (US)

( * ) Notice: Subject to any disclaimer, the term of this patent is extended or adjusted under 35 U.S.C. 154(b) by 150 days.

(21) Appl. No.: 14/852,874

(22) Filed: Sep. 14, 2015

(65) Prior Publication Data

US 2017/0071198 A1 Mar. 16, 2017

(51) Int. Cl.
*A01N 33/12* (2006.01)
*A01N 55/00* (2006.01)

(52) U.S. Cl.
CPC ............ *A01N 55/00* (2013.01); *A01N 33/12* (2013.01)

(58) Field of Classification Search
CPC ......... A01N 55/00; A01N 65/36; A01N 33/12
USPC ............................................ 424/426; 514/63
See application file for complete search history.

(56) References Cited

U.S. PATENT DOCUMENTS

| | | | |
|---|---|---|---|
| 2,005,008 A | 6/1935 | Schaer |
| 3,560,385 A | 2/1971 | Roth |
| 3,730,701 A | 5/1973 | Isquith et al. |
| 3,794,736 A | 2/1974 | Abbott et al. |
| 3,860,709 A | 1/1975 | Abbott et al. |
| 3,865,728 A | 2/1975 | Abbott et al. |
| 4,005,025 A | 1/1977 | Kinstedt |
| 4,005,028 A | 1/1977 | Heckert et al. |
| 4,005,030 A | 1/1977 | Heckert et al. |
| 4,161,518 A | 7/1979 | Wen et al. |
| 4,282,366 A | 8/1981 | Eudy |
| 4,361,273 A | 11/1982 | Levine et al. |
| 4,393,378 A | 7/1983 | Danielsen et al. |
| 4,394,378 A | 7/1983 | Klein |
| 4,406,892 A | 9/1983 | Eudy |
| 4,421,796 A | 12/1983 | Burril et al. |
| 4,467,013 A | 8/1984 | Baldwin |
| 4,564,456 A | 1/1986 | Homan |
| 4,567,039 A | 1/1986 | Stadnick et al. |
| 4,615,882 A | 10/1986 | Stockel |
| 4,682,992 A | 7/1987 | Fuchs |
| 4,781,974 A | 11/1988 | Bouchette et al. |
| 4,797,420 A | 1/1989 | Bryant |
| 4,842,766 A | 6/1989 | Blehm et al. |
| 4,847,088 A | 7/1989 | Blank |
| 4,908,355 A | 3/1990 | Gettings et al. |
| 5,013,459 A | 5/1991 | Gettings et al. |
| 5,411,585 A | 5/1995 | Avery et al. |
| 5,468,725 A | 11/1995 | Guenin et al. |
| 5,660,891 A | 8/1997 | Kenyon et al. |
| 5,719,114 A | 2/1998 | Zocchi et al. |
| 5,954,863 A | 9/1999 | Loveless et al. |

(Continued)

FOREIGN PATENT DOCUMENTS

| | | |
|---|---|---|
| CA | 1217004 | 1/1987 |
| EP | 2460409 | 6/2012 |

(Continued)

OTHER PUBLICATIONS

Sabine, J.R., et al. "Laboratory Evaluation of some Marine Plants on South Australian Beaches." J. Agric. Sci. Technol. (2001), vol. 3: pp. 91-100.
A. J. Asquith; Surface-Bonded Antimicrobial Activity of an Organosilicon luaternary Ammonium Chloride; Copyright 1973 American Society of Microbiology; Applied Microbiology, Dec. 1972 p. 859-863, vol. 24, No. 6.
Traber, M.G., et al. "Vitamin E: function and metabolism," FASEB Journal. (Jul. 1999), vol. 13, pp. 1145-1155.
Google Search—jp 2091008—related patents, (the second being U.S. Pat. No. 8,541,610, No. 42 on this list).

*Primary Examiner* — Yanzhi Zhang

(74) *Attorney, Agent, or Firm* — Tuggle Duggins P.A.; Blake Hurt

(57) ABSTRACT

This invention is a process for the manufacture of water stable, partially polymerized antimicrobial silanol quaternary ammonium compounds (SQACs) and their trisilanol, polysiloxanol and water soluble polysiloxane derivatives thereof. Partial polymerization is accomplished by allowing the aqueous SQAC product solution to polymerize at conditions that will substantially convert all the chlorosilanol monomer to a copolymer of the SQAC, thus reducing the toxicity of the solution greatly. A stabilizing agent is added either before or after the partial polymerization. The stabilizing agent is selected from a list of antimicrobial, naturally occurring, renewable phytochemical essential oils and extracts that easily form crystal clear microemulsions when water is added to the concentrated SQAC/essential oil mixture. These non-foaming oil in water microemulsions have excellent long term storage stability, are freeze/thaw stable, remain very low in viscosity and do not phase separate or precipitate for many months. Many of the essential oils found to be useful in this process are non-toxic food additives and have pleasant scents, have low flammability yet are volatile enough to evaporate upon cure down of the SQAC, thereby resulting in a higher concentration of SQAC in the cured, antimicrobial film. Economically shippable concentrations of the low toxicity, partially polymerized, stabilized SQACs can be further diluted with water to application concentrations without losing any of their stabilizing properties and remain storage stable at these lower concentrations indefinitely. In particular, the invention relates to the use of such aqueous dilutions cured as durable antimicrobial coatings on both manufactured and natural substrates and for human or animal skin that covalently bond to the skin, remain active through many washings and reduce or eliminate bacteria, viruses and fungi for days.

16 Claims, No Drawings

(56) References Cited

U.S. PATENT DOCUMENTS

| | | |
|---|---|---|
| 5,954,869 A | 9/1999 | Elfersy et al. |
| 5,959,014 A | 9/1999 | Liebeskind et al. |
| 6,110,474 A | 8/2000 | Roman |
| 6,235,298 B1 | 5/2001 | Naser et al. |
| 6,376,696 B1 | 4/2002 | Raab et al. |
| 6,384,003 B1 | 5/2002 | Julemont |
| 6,451,755 B1 | 9/2002 | Norman |
| 6,613,755 B2 | 9/2003 | Peterson et al. |
| 6,632,805 B1 * | 10/2003 | Liebeskind ............ A01N 55/00 106/15.05 |
| 8,541,610 B2 | 9/2013 | Taralp |
| 8,921,303 B1 | 12/2014 | Lull et al. |
| 9,089,138 B2 | 7/2015 | Higgins et al. |
| 2003/0114345 A1 | 6/2003 | Leonard et al. |
| 2005/0008613 A1 | 1/2005 | Peterson et al. |
| 2006/0115440 A1 | 6/2006 | Arata et al. |
| 2006/0193816 A1 | 8/2006 | Elfersy et al. |
| 2007/0021383 A1 | 1/2007 | Loder |
| 2007/0161526 A1 | 7/2007 | Vlad et al. |
| 2007/0237901 A1 | 10/2007 | Moses et al. |
| 2008/0181862 A1 | 7/2008 | Chisholm et al. |
| 2010/0028462 A1 | 2/2010 | Bolkan et al. |
| 2010/0167613 A1 | 7/2010 | Higgins et al. |
| 2011/0233810 A1 * | 9/2011 | Neigel ................... A01N 33/12 264/83 |
| 2012/0149623 A1 | 6/2012 | Li et al. |
| 2013/0030207 A1 | 1/2013 | Taralp |
| 2015/0182446 A1 | 7/2015 | Fenyvesi et al. |

FOREIGN PATENT DOCUMENTS

| | | |
|---|---|---|
| GB | 1386876 | 3/1975 |
| WO | 1997-041729 | 11/1997 |
| WO | 2000-078770 | 12/2000 |
| WO | 2007-133934 | 11/2007 |
| WO | 2011-119237 | 9/2011 |
| WO | 2011-123623 | 10/2011 |
| WO | 2013-075921 | 5/2013 |
| WO | 2015-002786 | 1/2015 |

* cited by examiner

PROCESS FOR THE PRODUCTION OF PARTIALLY POLYMERIZED ANTIMICROBIAL SILANOL QUATERNARY AMMONIUM COMPOUNDS

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO SEQUENCE LISTING, A TABLE OR A COMPUTER PROGRAM LISTING COMPACT DISK APPENDIX OR A DESCRIPTION OF DRAWINGS

Not applicable

TECHNICAL FIELD OF THE INVENTION

The present invention relates to silanol quaternary ammonium compounds (SQACs) and a process for controlling the viscosity and lowering the toxicity of aqueous dilutions of SQACs using naturally derived, renewable phytochemical, essential oils or extracts. In particular, the invention relates to the use of such aqueous dilutions as antimicrobial agents used to protect both manufactured and natural substrates from microbial growth.

BACKGROUND OF THE INVENTION

A biocide is any substance that kills microorganisms such as bacteria, molds, algae, fungi or viruses. A biostatic is any substance that inhibits the growth of these organisms. The collective group is called antimicrobials. People have been utilizing antimicrobials, commonly called preservatives, since they first discovered a need to extend the useful life of their food as well as their possessions. Sea salt may have been the first antimicrobial used to preserve food. The mummification techniques employed by early Egyptians used to preserve the human and animal body used salts and a variety of resins. These preservatives were thought to possess magical powers, as well as the ability to install qualities of eternal life.

The existence of microorganisms in nature was discovered in the late 1600s with the invention of the microscope. As early as 1705, mercuric chloride was used to preserve ships' planking against shipworm. It was not until the 19th century discoveries by Pasteur, Gram and others that the causative agents of microbiological deterioration were understood, although use of antimicrobials in a cause and effect relationship with microorganisms is less than a century old.

It is well known in the art that certain silanol quaternary ammonium compounds possess bacteriostatic, fungistatic and algaestatic and/or bactericidal, fungicidal and algaecidal properties. See, for example, U.S. Pat. Nos. 3,730,701; 3,817,739; and 4,394,378; and British Patent No. 1,386,876. For example, one such compound, 3-(trimethoxysilyl)propyl octadecyldimethyl ammonium chloride is a commercial antimicrobial product marketed by Dow Corning as "Bioguard Q 9-5700" (EPA No. 34292-1). U.S. Pat. No. 3,794,736 describes a number of other organosilicon amines and salts thereof exhibiting antimicrobial activity on a wide variety of microorganisms.

SQAC antimicrobial technology utilizes the properties of reactive silanols and their ability to bond with a target surface. The reactive silanol will form a covalent bond with any surface containing oxygen, nitrogen or carbon in any form. For example hydroxides or oxides on the surfaces of metals (including stainless steel) will form a durable bond. In addition, silanol groups will homopolymerize via a condensation mechanism to form a durable, 3 dimensional crosslinked polymer matrix. The application is therefore very versatile and many types of surfaces may be treated, such as plastic, metal, fabric, tile, masonry, vinyl, wood, painted surfaces and human and animal skin, hair and nails.

The silanols are modified with biocidal adjuncts in the form of alkyl quaternary ammonium groups, so that when the silanols fix onto a surface, the active biocidal sites become fixed too. The films created are extremely thin, between 15 nm and 180 nm, and therefore the original physical properties of the surface are little affected.

Bacteria arriving on the surface encounter the hydrocarbon portion of the biocidal adjunct that may be assimilated into the cell without any disruption. However, contact with the positively charged nitrogen atom will unbalance the electrical equilibrium within the porin channels and on the outer protein layers such that the cells can no longer function correctly and the microbes will die without electron transfer. Therefore the positively charged nitrogen is immediately prepared to subsequently kill additional microbes. Since the kill is electrical and not poison, SQACs do not produce new, resistant strains of microbes such as MRSA.

The fixed nature of the SQAC biocide is important where toxicity, taint and other organoleptic aspects are of concern. This bactericidal surface treatment is not removed by normal cleaning procedures. In fact, it is important to maintain the normal cleaning regime in order to 'refresh' the biocidal surface. The thinness of the film enables application in areas where optical properties are important such as treatment of contact lenses. The technology has been used for treatment of bed sheets, hospital garments (Murray et al, 1988), curtains, floor and wall materials, air filtration systems, medical devices, bandages, surgical instruments and implants (Gottenbos et al, 2002). The technique has been used to prevent biofilm growth on catheters, stints, contact lenses and endotracheal tubes.

Hospital Acquired Infections are responsible for 100,000+ deaths per year in the United States alone. The SQAC technology is used to treat human skin where the SQAC covalently bonds to form a durable, antimicrobial barrier that lasts through many washes and provides up to 3 days of reduction or elimination of bacteria, viruses and fungi including the following non-limiting specific list of microbes (Peterson et al, 2003):
Bacteria:
Gram Positive Bacteria:
*Citrobacter freundii*
*Citrobacter diversus*
*Corynebacterium diptheriae*
*Diplococcus pneumoniae*
*Micrococcus* sp. (I)
*Micrococcus* sp. (II)
*Micrococcus* sp. (III)
*Mycobacterium* spp.
*Staphylococcus albus*
*Staphylococcus aureus*
*Staphylococcus citrens*

*Staphylococcus epidermidis*
*Streptococcus faecalis*
*Streptococcus pyogenes*
Gram Negative Bacteria:
*Acinetobacter calcoaceticus*
*Enterobacter aerogenes*
*Enterobacter agiomerans* (I)
*Enterobacter aglomerans* (II)
*Escherichia*
*Klebsiella pneumoniae*
*Nisseria gonorrhoeae*
*Proteus mirabilis*
*Proteus morganii*
*Proteus vulgaris*
*Providencia* spp.
*Pseudomonas*
*Pseudomonas aeruginosa*
*Pseudornonas fragi*
*Salmonella choleraesuis*
*Salmonella enteritidis*
*Salmonella gallinarum*
*Salmonella paratyphi A*
*Salmonella schottmuelleri*
*Salmonella typhimurium*
*Salmonella typhosa*
*Serratia marcescens*
*Shigella flexnerie* Type II
*Shigella sonnel*
*Virbrio cholerae*
Viruses:
Adenovirus Type IV
*Feline Pneumonitis*
Herpes Simplex Type I & II
HIV-1 (AIDS)
Influenza A (Japan)
Influenza A2 (Aichi)
Influenza A2 (Hong Kong)
Parinfluenza (Sendai)
Poliovirus
Reovirus
Respiratory Synctia
Fungi and Mold:
*Alternaria altemata*
*Asperigillus niger*
*Aureobasidium pullulans*
*Candida albicans*
*Cladosporium ciadosporioides*
*Drechslera australiensis*
*Gliomastix cerealis*
*Microsporum audouinii*
*Monilia grisea*
*Phoma fimeti*
*Pithomyces chartarurn*
*Scolecobasidium humicola*
*Trychophyton interdigitale*
*Trychophyton Mentagrophytes*

The EPA's 2007 toxicity ruling on SQAC in the same EPA's Pesticide Docket # EPA-HQ-OPP-2007-0831 states "Upon reviewing the available toxicity information, the Agency has concluded that there are no endpoints of concern for repeated oral or dermal exposure to the trimethoxysilyl quats. This conclusion is based on low toxicity observed in acute, subchronic and developmental studies conducted with the trimethoxysilyl quat compounds. There are no concerns for carcinogenicity for the trimethoxysilyl quats based on the results of the mutagenicity studies and the lack of any systemic toxicity being observed in the toxicity data base; therefore, no carcinogenic analysis is required."

The EPA's 2007 environmental fate ruling on SQAC as stated in EPA's Pesticide Docket # EPA-HQ-OPP-2007-0831 states "The Agency has conducted an environmental fate assessment dated Sep. 19, 2007 for the trimethoxysilyl quats. The hydrolysis data indicate that the trimethoxysilyl quats are soluble but not stable in water. Environmental fate studies for the trimethoxysilyl quats consist of only a hydrolysis study and it was concluded by the Agency that no further fate studies would be required because of the instability of the compounds and their formation of an insoluble silane degradate. The trimethoxysilyl quats are not expected to contaminate surface or ground water due to rapid degradation by hydrolysis."

For health, safety and economical reasons, it is most desirable to apply such antimicrobial SQACs from an aqueous medium, which may contain additives and components the purpose of which is to increase long term aqueous storage stability against homopolymerization of the hydrolyzed silanol groups causing viscosity increase and/or precipitation, provide scent and maintain solution clarity, improve performance and protect against aqueous mold growth.

Imparting long-term storage stability, however, to the newly formed aqueous SQAC solution, is a major concern that directly impacts the use and marketability of such antimicrobial formulations. Experience has shown that even low aqueous concentrations are unstable, leading to the premature sedimentation of polysilsesquioxane-type polymers or to rapid increases in solution viscosity causing disruption to standard methods of coating applications. To improve shelf-life and storage stability, thus yielding a marketable formulation, many strategies have been implemented.

DESCRIPTION OF PRIOR ART

Some of the common approaches utilized in order to extend storage life of aqueous SQACs have been to introduce surfactant additives, to coordinate the free silanol end groups with stabilizers such as simple sugars and other multiple hydroxyl group molecules, to coordinate/associate said quaternary organosilane hydrolysates with hydrophilic polymers, to incorporate non-aqueous solvents such as the toxic methanol and methyl or butyl cellosolve, to use alternative aqueous/organic systems, and to apply combinations thereof. In some cases, pH adjustments have been used to maximize the benefits imparted by a stabilizer. The implementation of such strategies has proved instrumental and necessary to yield marketable water-based formulations.

It is desirable to employ additives that will evaporate completely during the coating and curing operation thus allowing the generation of a high degree of homo polymer crosslinking of the silanol groups providing a highly water and solvent insoluble coating on the substrate. Non-volatile additives, especially hydrophilic additives, that retard polymerization of aqueous solutions may also retard this degree of crosslinking needed during the cure of the film, making this antimicrobial coating more susceptible to greater rate of loss in applications where water comes in frequent contact with the cured film. In addition, non-volatile additives that become part of the cured film will decrease the cationic charge density which may lead to inferior antimicrobial efficacy.

The following patents and patent applications teaching stabilization of aqueous SQACs are incorporated herein for reference. U.S. Pat. No. 6,376,696 and WO00/78770 outline a process to prepare a quaternary ammonium silane from tetradecyldimethylamine and 3-chloropropyltrimethoxysilane, in which the yield during quaternization is quantitative and the product is dissolved and stabilized in an aqueous solution containing methyl triglycol as active stabilizer, however this stabilizer both hydrophilic and non-volatile.

U.S. Pat. No. 3,560,385 outlines to a process to prepare a quaternary ammonium silane from octadecyldimethylamine and 3-chloropropyltrimethoxy silane in methyl cellosolve. The yield of quaternization is near quantitative and said product is easily dissolved and retained in water by virtue of methyl cellosolve, acting as active stabilizer, however methyl cellosolve is quite toxic and hydrophilic.

U.S. Pat. No. 6,613,755 outlines a process to dissolve methanolic solutions of quaternary amines in water, giving an overall very low concentration of the antimicrobial with respect to the final water/methanol solution. However, shipping such low concentrations is very uneconomical and methanol is toxic.

U.S. Pat. No. 6,632,805 and WO97/41729 relate to a process to prepare a quaternary ammonium silane from octadecyldimethylamine and 3-chloropropyltrimethoxysilane. In following a process, which implements pH control and the addition of an active stabilizer, a stable solution of the trioxasilylbicycloctyl intermediate species is obtained. Stabilizers included pentaerythritol, tris(hydroxymethyl)ethane, tris(hydroxymethyl)methane, and similar compounds. Such compounds, although good stabilizers for aqueous SQACs are hydrophilic and quite non-volatile and may be incorporated into the cured film and may reduce the charge density and antimicrobial efficacy as well as water resistance.

US20080181862 relates to the preparation of an antimicrobial polysiloxane. As part of this embodiment, a dimethylaminopropyl organosilane is quaternized using an alkyl halide and the ensuing product is solvated in methanol but not water, yielding large amounts of toxic methanol being released during cure.

US2010/0028462 relates to the preparation of a water-stable quaternary ammonium organosilane hydrolysate. Here, the key to retaining stability is the incorporation of a hydrophilic, non-ionic surfactant. Although good stability is obtained, such mixtures may foam badly during application and may require a post treatment wash to remove the surfactant since most non-ionic surfactants lack any volatility.

U.S. Pat. No. 4,842,766 relates to clear microemulsions of SQACs and water in wt ratios of 1/99 to 99/1 using a cosurfactant selected from a group having an HLB of >1. Specific examples are propylene glycol, ethylene glycol, pentanol, decanol, and glycerol. However, the concentrated SQAC needs to contain low levels methanol in order for the microemulsion to form.

U.S. Pat. No. 6,613,755 relates to stable aqueous solutions of SQACs in distilled or deionized water when measured conductively has an electrical resistance of at least 10 megohm per square centimeter with a purity level of 18 megohm per square centimeter being preferred. However, the authors admit the presence of dissolved impurities such as metal ions, metal salt and anionic species, particularly fluoride ions will greatly decrease the stability and shelf life of the aqueous formulations. Thus, any downstream contamination of this type will cause this unstabilized formulation to spoil.

The above patents and applications along with many others not referenced, demonstrate there is a clear and present need to discover a class of stabilizers having all of the following attributes:

1) Low Toxicity 2) Low Flammability 3) Excellent control of aqueous solution viscosity of SQACs 4) Pleasant scent 5) Volatility (little or no incorporation of the stabilizer into the cured film) 6) Antimicrobial Activity 7) Obtained from a renewable resource Unexpectedly, a unique group of viscosity stabilizing compounds has been discovered that satisfies all 7 of the above attributes needed to correct the shortcomings of previous inventions of this type. These unique stabilizers are certain naturally derived, renewable, phytochemical essential oils that have been proven to possess low toxicity, low flammability, excellent stabilization of aqueous SQACs, pleasant scent, good volatility, and demonstrate antimicrobial activity of their own.

Another objective of this invention is to further purify residual monomeric reactants from aqueous solutions of SQACs. It is common practice among producers of these compounds to use as starting materials for their synthesis a tertiary amine such as octadecyldimethylamine and an aliphatic chlorosilanol such as chloropropyptrimethoxy silane (CPTMS), where the chlorosilanol is used in excess to drive the reaction to completion. Typical excesses of CPTMS currently used in the industry range from 3% to 30% by weight resulting in similarly high residual monomeric CPTMS left in the product solution.

Dow Corning Corporation, a producer of both CPTMS and SQACs, lists in their CPTMS material safety data sheet a 0.1 part per million time weighted average (TWA) for human exposure. Although CPTMS is expected to hydrolyze in an aqueous solution from the trimethoxy to the trihydroxy moiety, there is insufficient data to determine the relative toxicity of the hydrolyzed form, and therefore must assume it to be similar in toxicity to its un-hydrolyzed precursor.

Biosafe, Inc. in Pittsburgh, Pa. has realized that high levels of residual monomeric reactants and the monomeric SQAC product have some toxicity associated with their use and countered this condition by offering an SQAC essentially free of both monomeric reactants and monomeric product. This is accomplished by polymerizing an aqueous solution containing both monomeric SQAC and residual monomeric reactants using various methods such as pH manipulation or addition of condensation polymerization catalysts, followed by isolation and purification of the resultant water insoluble polymer. Biosafe claims both lower toxicity and improved antimicrobial efficacy compared to using the current monomeric SQAC products available in today's market. See for example U.S. Pat. No. 7,851,653.

Although the Biosafe product may be less toxic to use compared to monomeric SQACs, the main issue is solubility of Biosafe product in water which is very low, even when the water is heated to effect solution. This low water solubility prevents its use in clear, aqueous consumer personal care products without the use of solubility aids such as organic co-solvents. Such co-solvents are finding less acceptance in today's marketplace as ever increasing importance is being placed on developing environmentally friendly, low VOC, naturally derived and renewable raw material sourced chemical products.

Therefore, there is clear and present need for a process to partially polymerize an aqueous solution of an SQAC and stop this polymerization at a point where the SQAC is a clear solution at 5-10% in water after it has hydrolyzed to the trihydroxy form, and where enough condensation polymerization has taken place to substantially convert all of the residual excess chlorosilanol from it monomeric form to a copolymer with the SQAC. Such partially polymerized solutions are less toxic to work with in application due to the much lower concentration of any monomeric chlorosilanol, producing lower atmospheric concentrations and lower user exposure to the chlorosilanol monomer.

Unexpectedly, it has been determined that partially polymerized solutions of SQACs are substantially free of monomeric chlorosilanol due to their ability to copolymerize in an approximately similar weight ratio of the monomeric SQAC and the monomeric chlorosilanol as they exist in the monomeric solution of the two components. For example, it has been experimentally determined from organic and ionic chloride measurements of partially polymerized SQAC aqueous product solutions that both undialyzed and dialyzed solutions (using a 3.5 k to 5.0 k Dalton molecular weight cutoff membrane) contain the approximately the same ratio of chlorosilane to SQAC. This is important because the excess chlorosilanol weight of SQAC products is always lower than the weight of the SQAC. When this product mixture is partially polymerized according to this unexpected discovery, substantially complete conversion of chlorosilanol monomer to a copolymer is obtained at a relatively low solution viscosity that retains excellent solubility, clarity and reactivity with substrates.

BRIEF DESCRIPTION OF THE INVENTION

This instant invention is a process for the manufacture of partially polymerized water stable antimicrobial silanol quaternary ammonium compounds where the stabilizing agent is chosen from the collective group of essential oils and extracts that are commonly obtained by steam distillation or cold pressing of stems, bark, leaves, fruit, peels and flowers of various plant species throughout the world. Some of the preferred essential oils used in the instant invention are derived from leaves that are edible herbs. Other preferred essential oils are extracted from the peels of citrus fruits that are used as flavorings for food and beverages. This source of stabilizing agents is plentiful, renewable and generally considered to have low toxicity to humans and animals. The process of this invention teaches the manufacture of crystal clear, water stabilized, partially polymerized SQAC microemulsions with essential oils that contain substantially no toxic monomeric chlorosilanol.

DETAILED DESCRIPTION OF THE INVENTION

For purposes of demonstrating the process of this invention, the follow SQAC compounds were selected as preferred examples:

SQAC #1 3-(trimethoxysilyl) propyl-N-octadecyl-N,N-dimethyl ammonium chloride
SQAC #2 3-(trimethoxysilyl) propyl-N-tetradecyl-N,N-dimethyl ammonium chloride
SQAC #3 3-(triethoxysilyl) propyl-N-octadecyl-N,N-dimethyl ammonium chloride
SQAC #4 3-(trimethoxysilyl) propyl-N-didecyl-N,N-dimethyl ammonium chloride SQAC #1 is commercially available from Indusco, Ltd in Greensboro, N.C. as Bioshield 7200 and is sold as a concentrated solution of the active ingredient in anhydrous methanol. A similar product is available from both Dow Corning, Microban International and others. Of the three selected SQAC compounds, SQAC #1 is the most preferred compound for demonstrating the process of this invention due to its high sales volume and popularity of use as an antimicrobial coating on a myriad of substrates.

The following, although illustrative of examples of antimicrobial phytochemical plant species whose essential oils and extracts that can be used in this invention, but is not meant to be an all-inclusive list:

*Jasonia candicans* (sesquiterpenes, lactones); *Polygonum flaccidum* (flavone and alpha santalene derivatives); *Acalypha wikesiana* (extracts); *Pavetta owariensis* (procyanidins); *Plectranthus hereroensis* (diterpenoids, diterpenes); Moss (Dicranin extract); *Cannabis sativa* (extract); *Gloiosiphonia* spp. (gloiosiphones); *Laminaceae* spp. (extract); *Securidaca* spp. (extract); *Veronia* spp. (extract); *Hyptis umbrose* (umbrosone); *Asclepias syriaca* (milkweed extract); *Tagetes tenuifolia* (thiophene); *Calophyllum inophylloide* (flavonoids); *Tanacetum densum* (sesquiterpene lactones, triterpenoids); *Neorautanenia mitis* (extract); *Premna schimper* (diterpene); *Premna oligotricha* (sesquiterpenes); *Premna oligotricha* (diterpenes); *Jasonia candicans* (essential oils); *Visnea mocanera* (beta-sitosterol, triterpenic betulinic acid, ursolic acid, plantanic acid); *Asteraceae* spp. (terthiophenes and polyynes); *Petalostemum purpureum* (extract); *Camelia sinensis* (catechin); *Helichrysum picardii* (flavonoids); *Helichrysum italicum* (flavonoids); *Corydalis pallida* (protoberberine alkloids); *Shiraia bambusicola* (perylenequinones); *Fraxinum omus* (hydroxycoumarins); *Podocarpus nagi* (totarol and nortiterpene dilactones); *Heterotheca inuloides* (sesquiterpenoids); *Pelargonium* spp. (essential oils); *Piper sarmentosum* (phenylpropanoids); *Allium* spp. (extract); *Juniperus procera* (diterpenes); *Achillea conferta* (flavonoids, flavones, sesquiterpenoid lactones); *Magnolia virginiana* (lignans, neolignans); *Eucalyptus euglobal* (euglobal); *Armillaria mellea* (armillaric acid); *Dracena mannii* (spirostanol saponin); *Piper aduncum* (chromenes, prenylated benzoic acid); *Rhamnaceae* spp. (cyclopeptide alkaloids); *Buddleja globosa* (verbascoside); *Cephalocereus senilis* (phytoalexin aurone); *Salvia albocaerulea* (diterpene); *Gomphrena martiana* and *Gomphrena boliviana* (extracts); *Paepalanthus* spp. (vioxanthin); *Helichrysum stoechas* and *Helichrysum crispum* (extracts); *Achillea ptarmica* (trans-pinocarveyl hydroperoxides); *Dehaasia incrassata* (alkaloids); *Asteraceae* spp. (extracts); *Arctotis auriculate* (extracts); *Eriocephalus africanus* (extracts): *Felicia erigeroides* (extracts); *Hemerocallis fulva* (phytosterols, fatty acid esters); *Psoralea juncea* (plicatin B); *Pluchea symphytifolia* (caffeic acid esters); *Tovomitopsis psychotrifolia* (Vitamin E derivative), *Celosia argentea* (triterpenoid saponins and flavonoids); *Azadirachta indica* (tetranortriterpenoid, mahmoodin, protolimonoids, naheedin); *Moraceae* spp. (coumarins); *Hypericum erectum* (phloroglucinol derivatives); *Podospora appendiculate* (Appenolides A, B, & C, furanones); *Artemisia princeps* var. *orientalis, Artemisia capillaris, Artemisia mexicana* and *Artemisia scoparia* (extract); Paddy malt (mash extract); *Kigelia pinnata* (extract); *Acalypha wilkesiana* (extract); seaweeds, seagrass and lemongrass (essential oils); *Borrieria latifolia, Borreria setidens, Hedyotis diffusa), Hedyotis nudicaulis, Morinda elliptica, Morinda umbellata, Sida rhombifolia*, and *Vitex ovata* (extracts); *Tabebuia impetiginosa, Achyrocline* spp., *Larrea divaricata, Rosa borboniana, Punica granatum, Psidium guineense, Lithrea ternifolia* (extracts); *Lepechinia caulescens, Lepidium virginicum* and *Tanacetum parthenium* (extracts); *Talaromyces flavus* (extracts); *Daucus carota* (extract); *Flabellia petiolata, Caulerpa prolifera, Halimeda tuna, Corallina elongata, Lithophyllum lichenoides, Phyl-*

*lophora crispa, Cystoseira* spp., *Halopteris* spp., *Codium* spp., *Valonia utricularis, Posidonia oceanica, Zostera noltil* and *Cymodocea nodosa* (extracts); *Centauraea orientalis, Diospyros khaki, Sida hermaphrodita, Forsythia intermedia, Scutellaria polydon, Eugenia malaccensis* and *Eugenia jambolana* (extracts); *Fritillaria* L. spp. (ebeinone, steroidal alkaloids); *Kigelia pinnata, Peperomia pellucida, Populus nigra, Populus balsamifera* and *Populus deltoides* (extracts); *Melaleuca alternifolia* (essential oil); *Elfvingia applanata* (naringenin); *Ficus sycomorus*, grapefruit seed, Garlic, Allicin, Peat, *Strophanthus hispidus, Secamone afzeli, Mitracarpus scaberi, Entada abyssinjca, Terminalia spinosa, Harrisonia abyssinica, Ximinea caffra, Azadirachta indica, Spilanthes mauritiana, Terminalia spinosa* (extracts); Cyanobacteria (ambigols A and B, tjipanazole); coffee (extract); *Sporochnus pedunculatus, Dalbergia melanozylon, Celastrus scandens, Juglans nigra, Kalmia latifolia, Pelargonium xhortorum, Rhus glabra* and *Lindera benzoin* (extracts); *Striga densiflora, Striga orobanchioides, Striga lutea, Pistacia lentiscus* L., *Mitracarpus villosus, Bixa orellana, Bridelia ferruginea, Alpinia katsumadai, Alpinia officinarum, Artemisia capillaris, Casia obtusifolia, Dendrobium moniliforme, Epimedium grandiflorum, Glycyrrhiza glabra, Lithosperum erythrorhizon, Magnolia obovata, Morus bonbycis, Natopterygii incisium, Polygonum multiflorum, Prunus mume, Rheum palmatum, Ricinus communis, Sophora flavescens, Swertia japonica*, black pepper, rosemary, red pepper, *Isopyrum thalictroides, Calotropis procera, Chrysanthemum* spp., *Holarrhena antidysenterica, Lunularia crusiata, Dumertiera hirsuta, Exormotheca tuberifera*, and liverwort (extracts); *Filipendula ulmaria, Salix glauca, Usnea filipendula, Clkadina arbuscula* (salicylic compounds); *Tanacetum parthenium, Thymus capitatus*, and *Elfingia applanata* (extracts); *Fraxinus ornus* (hydroxycoumarins, esculin, esculetin, fraxin, and fraxetin); *Zizyphus nummularia*, LONGO VITAL, *Pelargonium* spp., *Scaevola sericea, Psychotria hawaiiensis, Pipturus albidis, Aleurites moluccana, Solanum niger, Piper methysticum, Barringtonia asiatica, Adansonia digitata, Harungana madagascariensis, Jacaranda mimosaefolia, Erythroxylum catauba, Bidens pilosa, Lemna minor, Potamogeton* spp., *Nasturtium officinale, Apium nodiflorum, Agaricus subrutilescens, Amanita virosa, Amanita pantherina, Lycoperdon perlatum, Psidium guajava, Averrhoa carambola, musa sapientum, Carica papaya, Passiflora edulis, Lansium domesticum* and *Baccaurea motleyana* (extracts); horse radish, celandine grass, bur marigold and yarrow grass (extracts); *Abuta grandifola, Cyperus articulatus, Gnaphalium spicatum, Pothomorphe peltata, Ficus sycomorus, Ficus Benjamina, Ficus bengalensis, Ficus religiosa, Alchornea cordifolia, Bridelia feruginea, Eucalyptus citriodora, Hymenocardia acida, Maprounea africana, Monachora arbuscula, Tedania ignis, Arenosclera* spp., *Amphimedon viridis, Polymastia janeirensis, Aplysina fulva, Pseudaxinella lunaecharta, Nelumbium speciosum* and *Mycale arenosa* (extracts); cloves (eugenol acetate and iso-eugenol); *Chrysthanemum boreale* (sesquiterpenoid lactones); *Eucalyptus globolus, Punica granatum, Bocconia arborea, Syzygium brazzavillense, Syzygium guineense, Carthamus tinctorius), Ginkgo biloba, Mosla chinensis, Salvia officinalis*, and *Cinnamomum cassia* (extracts); *Cryptolepis sanguinolenta* (alkaloids, cryptolepine); *Chelidonium majus* (alkaloids, berberine, coptisine); *Vitex agnus-castus* (extract); *Cladonia substellata* (usnic acid); *Fuligo septica, Tubifera microsperma* (extract); *Mundulea monantha, Tephrosia linearis* (flavonoids); *Lpomoea fistulosa* (extract); *Pimenta dioica* (essential oils); *Ratibida latipalearis, Teloxys graveolens, Dodonaea viscosa, Hypericum calycinum, Hyptis albida, Hyptis pectinata, Hyptis suaveolens* and *Hyptis verticillata* (extracts); *Asteriscus graveolones* (bisabolone hydroperoxides); *Derris scandens, Alnus rubra*, Araliaceae family (extracts); *Vinca rosea*, Australian tea tree oil, peppermint oil, sage oil, thyme oil, thymol, grapefruit oil, lemon oil, lime oil, orange oil, tangerine oil, cedarwood oil, pine oil and d-limonene, eugenol and *Thuja orientalis* (extracts); *Anacardium occidentale* (phenolic lipids); *Oidiodendron tenuissimum* (extract); *Acacia nilotica* and *Acacia farnesiana* (polyphenol, tannin); *Teminalia alata* and *Mallotus phillipinensis* (extracts); *Piectranthus grandidentatus* (abientane diterpenoids); *Pumica granatum* and *Datura metel* (extracts); tea, *Agave lecheguilla, Chamaesyce hirta, Baccharis glutinosa* and *Larrea tridentata* (extracts); *Camelia sinensis* and *Euphorbia hirta* (theaflavin, polyphenon 60); *Tabernaemontana pandacaqui, Yucca shidigera, Hemistepa lyrata, Yougia japonica, Prunella vulgaris, Lamium amplexicaule, Juniperus chinensis, Ixeris dentata, Gnaphalium affine, Chelidonium majus, Spirea prunifolia, Erythronium japonicum, Taxus wallichiana, Ganoderma lucidum Drava nemorosa, Youngia capillaris, Equisetum arvense*, Australiam Lavender, Black Seed, *Catuaba casca*, Cineole, Damiana, *Dicranum scoparium*, Eucalyptus oil, Ginger, and Grape seed (extracts); Neem seed, bark, and leaf extract; Neem oil; New Zealand Manuka extract; Nicotiana tabacum extract; olive leaf extract; a-pinene and b-pinene extracts; Rhubarb root extract; *Syringa vulgaris* extract.

For purposes of demonstrating the process of this invention, preferred essential oils that have biocidal activity and form crystal clear microemulsions with aqueous SQACs are the essential oils of tea tree, peppermint, thyme, grapefruit, lemon, lime, orange, tangerine, cedarwood and pine and orange peel extract d-limonene.

The process of the instant invention produces novel, crystal clear, viscosity stable, partially polymerized oil-in-water microemulsions using SQACs, phytochemical extracts or essential oils, and distilled or deionized water. Microemulsion technology has been in existence for many years. In fact many commercial microemulsion products are found in the marketplace including floor polishes and cleaners, personal care products, pesticide delivery systems, cutting oils and drug delivery systems. Microemulsions are crystal clear because the micellar particle size is too small to scatter visible light. The IUPAC definition of microemulsion is "a dispersion of water, oil and surfactant(s) that is an isotropic and thermodynamically stable system with dispersed domain diameter varying approximately from 1 to 100 nm, usually 10 to 50 nm." The aqueous phase may contain salts or other ingredients such as polar solvents, and the oil may be a complex mixture of organic compounds. In contrast to ordinary, white macroemulsions that usually require high shear conditions to form, microemulsions form upon simple mixing of the components.

Unexpectedly, the SQAC which not only is the active ingredient producing durable antimicrobial films when cured, also does double duty as the only required surfactant needed to form the microemulsion with phytochemical essential oils and extracts. Such microemulsions need only standard mixing requirements such as those found in low speed mixing vessels, not high shear equipment such as various types of high speed or high pressure homogenizers. These microemulsions have been developed on lab scale using only the shear of low speed magnetic stirring bar mixing.

It has been determined that when preparing these microemulsions, order of addition is quite important. The SQAC is first to be added to the mixing vessel as a concentrated solution in the reaction solvent, followed by adding the essential oil or extract which dissolves in the concentrated SQAC to form a low viscosity, easily mixable, clear solution. The addition of the essential oil or extract will lower the temperature at which partial insolubility of the SQAC occurs, similarly to what would be expected if more reaction solvent was added. Mixtures of SQAC and essential oil or extract have been stored at room temperature for several months and show no signs of precipitation, loss of activity, color change or their ability to form microemulsions when additional water is mixed in.

To accomplish the process of making a crystal clear, viscosity stable microemulsion, all that is needed is the addition of distilled or deionized water to the SQAC/essential oil or extract solution that is under moderate agitation. Depending upon the type of SQAC and essential oil or extract being used, it was found that water heated above room temperature produces clear microemulsions more quickly. Preferred water temperature depends in part on the boiling point of the SQAC/essential oil/polar solvent mixture being treated based on safety considerations.

The rate of water addition is also dependent upon the components being used. Some systems allow water addition rates as rapid as less than one minute, while other systems require a water addition rate that will maintain a clear microemulsion mixing in the vessel. Microemulsion systems will maintain this clear appearance throughout the water addition process. This is the "best mode" for carrying out the process of this invention. If any turbidity of the mixing vessel contents occurs, there is a good chance a microemulsion will not be formed to completion resulting in less than crystal clarity of the final dispersion. Cloudy microemulsions may be repaired to form clear microemulsions by post heating the fully diluted microemulsion, then stopping the agitation and allowing the microemulsion to slowly cool to room temperature.

The rate of polymerization of an unstabilized or stabilized aqueous SQAC solution depends on the following variables: SQAC concentration, pH, residual reactants concentration, temperature, divalent anion concentration and water conductivity. There is a direct effect between these variables and the rate of polymerization. The higher the number for each of these variables, the faster the polymerization rate will be. The concentration of essential oil stabilizers in an aqueous SQAC microemulsion will have inverse effect on the rate of polymerization. The lower the essential oil concentration, the faster the rate of polymerization will be.

Rate of polymerization becomes important when producing partially polymerized aqueous solutions for the purpose of converting substantially all of the residual excess chlorosilanol monomer into a co-polymer with SQAC. The polymerization rate needs to be slow enough to be able to stop the polymerization at the point of very low residual excess chlorosilanol monomer yet rapid enough to be commercially economical. To this end several techniques have been employed. Raising the storage temperature, the pH and the SQAC concentration are 3 variables that work well to raise the polymerization rate, especially the rate of essential oil stabilized aqueous microemulsions. Additionally, these variables are easy to reverse when the desired degree of partial polymerization has occurred. Thus, lowering the storage temperature, lowering the pH and diluting the concentration will stop or severely retard the rate of polymerization.

The preferred process to produce commercial quantities of partially polymerized, crystal clear microemulsions is to premix the selected essential oil and Bioshield 7200, then add enough warm distilled water to make a >5% to 12% concentration of active SQAC. At these high concentrations even essential oil stabilized microemulsions will partially polymerize quickly yet controllably to allow quick stoppage of the polymerization by merely adding dilution water to a concentration of 5% or less active SQAC. With this method there is no pH adjustment and no additional salt created from it. This is the best mode of operation to facilitate the process of this instant invention.

Alternately, the addition of an aqueous SQAC microemulsion that has been stabilized by preferred essential oils, then partially polymerized at elevated temperature, and/or pH, when added to an unstabilized aqueous solution that has partially polymerized will effectively stop or at least severely retard the polymerization rate at room temperature.

Using a $3^{rd}$ method, the essential oil can be added to the partially polymerized SQAC as an oil-in-water microemulsion using a suitable surfactant system instead using the SQAC to facilitate the formation of the microemulsion. For example, decyl glucoside is widely used in skin care formulations to make crystal clear microemulsions of essential oils in water. Such microemulsions can be formed to contain >10% essential oil and can be used immediately, eliminating the need to wait for partial polymerization to take place, as is the case when using SQAC to form the microemulsion.

A $4^{th}$ method to partially polymerize SQAC is to add 2 to 6 parts of distilled water to 100 parts of a concentrated methanolic solution of SQAC and allow limited hydrolysis to take place. The hydroxysilyl groups will then start to partially polymerize to form a copolymer of SQAC and chlorosilanol. The degree of polymerization is limited by the amount of water added and these mixtures of oligomeric silane structures are then stable indefinitely. Essential oil stabilizers can be added either before or after the partial polymerization takes place.

The process of the instant invention produces a unique SQAC product in the industry today, containing substantially no toxic excess residual cholorsilanol monomer, yet remains a crystal clear, stable microemulsion when further diluted to application concentrations all the way down to 0.01%. Although the product of this improved process can be used in a broad range of applications including the manufacturing, construction, building maintenance and textile industries, the high purity and crystal clarity of the product are ideally suited for use in durable (persistent) hand sanitizers where monomeric residual chlorosilanol is simply unacceptable.

Especially adaptable are the currently marketed hand sanitizers based on benzalkonium chloride (BAC) as the active ingredient. Compatibility studies have been run by adding an essential oil stabilized, partially polymerized solution of 6% aqueous SQAC to 4 of the current best selling foaming hand sanitizers (FHS) including Vi-Jon's Germ-X, Pacific World's Handclens, KAS Direct's BabyGanics "The Germinator", Nehemiah Manufacturing's Kandoo and Walmart's Equate which is advertized as a foaming hand wash. All four brands have 0.10% to 0.13% BAC as the active ingredient. The active SQAC concentration added to these existing brands was 0.18% based on total weight of the hand sanitizer solution, done by adding 3% of the weight of the foaming hand sanitizer as a 6% aqueous, partially polymerized SQAC. The turbidity of the sanitizer solution was checked before and after the SQAC was added using a Hach Ratio Turbidimeter with the following results:

Germ-X had a turbidity of 1.06 Nephelos Turbidity Units (NTU) before the partially polymerized SQAC was added and 1.49 NTU after addition for no noticeable visual gain in turbidity.

Handclens had a turbidity of 2.14 NTU before the partially polymerized SQAC was added and 2.74 NTU after addition for no noticeable visual gain in turbidity.

BabyGanics "The Germinator" had a turbidity of 1.06 NTU before the partially polymerized SQAC was added and 1.49 NTU after addition with no noticeable visual gain in turbidity.

Nehemiah's Kandoo had a turbidity of 12.5 NTU before the partially polymerized SQAC was added and 9.1 NTU after addition with no noticeable visual increase in turbidity.

Walmart's Equate had a turbidity of 9.69 NTU before the partially polymerized SQAC was added and 10.35 NTU after addition with no noticeable visual increase in turbidity.

After several weeks aging at 25 C, there was no change in the turbidity of the above SQAC dosed products or any precipitation of any kind. An evaluation of the foam consistency was done by pumping one pump stroke of foam into the palm of a hand and inverting the hand so as to face the foam downward toward the floor. In all 5 of the sanitizers tested, both before and after adding the partially polymerized SQAC, 100% of the foam adhered to the downward facing palm for more than 10 seconds.

EXAMPLES

The present inventions can best be understood after a review of the following non-limiting examples:

Example #1

Into another 8 oz. glass jar was weighed 16.67 g of Bioshield 7200 (72% active SQAC) followed by 3.60 g of lemon essential oil and stirred on a magnetic stirring plate until the two components were clear and uniform (~1 min). With continued moderate stirring, 99.73 g of distilled water at a temperature of 35 C to 45 C was rapidly poured into the jar. Stirring was continued as the transparent concentrate slowly dissolved in the water to form a stabilized, crystal clear microemulsion of lemon oil in a 10.0% active Bioshield continuous phase. Brookfield viscosity of the freshly prepared microemulsion was measured at 10 cPs at 25 C and the pH was measured at 3.7. The 10% concentration SQAC prepared above was aged at 25 C for 3 days until the viscosity had risen to 46 cPs. A small sample was dialyzed using a 3.5K-5.0K Dalton molecular weight cut off (MWCO) membrane. The yield of retained SQAC that did not pass thru the membrane was 97.6%. The organic chloride (chlorosilane) to ionic chloride (SQAC) ratio of the partially polymerized, dialyzed solution and the monomeric, undialyzed sample were equal at 16.7% chlorosilane based on weight of SQAC present, proving that no monomeric chlorosilanol was present and all of it had polymerized to a harmless copolymer of SQAC. At this point additional distilled water was added to dilute the concentration of SQAC in the stabilized microemulsion to 5%. The viscosity of the crystal clear diluted microemulsion was 10 cPs and stayed the same for >6 months.

Example #2

Into an 8 oz. glass jar was weighed 16.67 g of Bioshield 7200 (72% active SQAC). With moderate stirring, 183.33 g of distilled water at a temperature of 35 C to 45 C was rapidly poured into the jar. Stirring was continued as the transparent concentrate slowly dissolved in the water to form an unstabilized, crystal clear solution of 6.0% active Bioshield in water. This solution was aged 13 days at 25 C until the solution had a viscosity of 46 cPs. Organic and ionic chloride analysis of the partially polymerized, dialyzed sample, when compared to the undialyzed monomeric starting solution showed that no volatile organic chloride was present in the partially polymerized sample indicating all monomeric chlorosilanol had copolymerized.

Into another 8 oz. glass jar was weighed 16.67 g of Bioshield 7200 (72% active SQAC) followed by 3.60 g of lemon essential oil and stirred on a magnetic stirring plate until the two components were clear and uniform (~1 min). With continued moderate stirring, 179.73 g of distilled water at a temperature of 35 C to 45 C was rapidly poured into the jar. Stirring was continued as the transparent concentrate slowly dissolved in the water to form a stabilized, crystal clear microemulsion of lemon oil in a 6.0% active Bioshield continuous phase. Brookfield viscosity of the freshly prepared microemulsion was measured at 10 cPs at 25 C and the pH was measured at 3.7. The pH was then raised to 5.0 using 1% sodium hydroxide in water and the crystal clear microemulsion was aged for 3 days at 25 C until the viscosity was 160 cPs, then the pH was adjusted down to 3.7 with 3.6% hydrochloric acid in water. With mixing, 50 g of this stabilized microemulsion was added to 200 g of an unstabilized, partially polymerized 6% solution in water The resultant microemulsion was crystal clear and had a viscosity of 40 cPs and a turbidity of 1.8 Nephelos Turbidity Units (NTU). A small sample of this mixture was dialyzed using a 3.5K-5.0K Dalton molecular weight cut off (MWCO) membrane. The yield of retained SQAC that did not pass thru the membrane was 100%. The undialyzed mixture was placed in a 25 C static oven and analyzed weekly for both viscosity increase (linear condensation polymerization) and development of insoluble precipitation (3 dimensional crosslinking) as measured by Hach Ratio Turbidimetry. After 3 months aging at 25 C this partially polymerized microemulsion sample was measured at 50 cPs and 2.4 NTU.

Example #3

Into an 8 oz. glass jar was weighed 16.67 g of Bioshield 7200 (72% active SQAC). With moderate stirring, 183.33 g of distilled water at a temperature of 35 C to 45 C was rapidly poured into the jar. Stirring was continued as the transparent concentrate slowly dissolved in the water to form an unstabilized, crystal clear solution of 6.0% active Bioshield in water. This solution was aged 13 days at 25 C until the solution had a viscosity of 50 cPs. Organic and ionic chloride analysis of a dialyzed sample indicated that no volatile organic chloride was present in the partially polymerized sample indicating all monomeric chlorosilanol had copolymerized. The partially polymerized solution of SQAC was then stabilized against further polymerization by addition of 3.6 g of lemon essential oil as a microemulsion in water using decyl glucoside as the surfactant. The jar was sealed and placed in a 25 C static oven and analyzed weekly for both viscosity increase (linear condensation polymerization) and development of insoluble precipitation (3 dimensional crosslinking) as measured by Hach Ratio Turbidimetry. After 3 months aging at 25 C this partially polymerized microemulsion sample was measured at 60 cPs and 2.8 NTU.

Example #4

Into an 8 oz. glass jar was weighed 19.91 g of Bioshield 7200 (72% active SQAC) followed by 3.375 g of lemon essential oil and stirred on a magnetic stirring plate until the two components were clear and uniform (~1 min). With continued moderate stirring, 0.71 g of distilled water at a temperature of 35 C to 45 C was rapidly poured into the jar. Stirring was continued as the transparent concentrate slowly dissolved in the water to form a stabilized, crystal clear microemulsion of lemon oil in a 58.5% active Bioshield continuous phase. Brookfield viscosity of the freshly prepared microemulsion was measured at 10 cPs at 25 C and the turbidity was 3.42 NTU. After aging overnight at 25 C the turbidity did not change. This concentrated microemulsion was then split in half and diluted to 6.0% active SQAC using two different dilution techniques; adding 40 C distilled water to the agitating concentrate and adding the concentrate to agitating 21 C distilled water. Both 6% microemulsions were then reheated to 82 C and allowed to air cool to RT resulting in clear microemulsions at 3.8 NTU and 4.0 NTU respectively. The viscosities of both were 40 cPs. A small sample of this mixture was dialyzed using a 3.5K-5.0K Dalton molecular weight cut off (MWCO) membrane. The yield of retained SQAC that did not pass thru the membrane was 97%. The undialyzed mixtures were placed in a 25 C static oven and analyzed weekly for both viscosity increase (linear condensation polymerization) and development of insoluble precipitation (3 dimensional crosslinking) as measured by Hach Ratio Turbidimetry. After 3 months aging at 25 C this partially polymerized microemulsion samples were both measured at 50 cPs and 4.0 NTU.

I claim:

1. A process to partially polymerize aqueous solutions of silanol quaternary ammonium compounds (SQACs) whereby substantially all the residual excess chlorosilanol monomer has polymerized to form a copolymer with the SQAC, and retard or stop the aqueous solution from further polymerization, further viscosity increases, and/or precipitation, the process comprising:
    preparing a mixture of anhydrous, concentrated SQAC (68 to 72% in methanol) with one or more renewable, naturally derived, antimicrobial, phytochemical essential oil or extract, then diluting the mixture to between 5%-12% of active SQAC with demineralized water to produce a crystal clear, stable microemulsion, that is then partially polymerized to a point whereby the residual excess chlorosilanol monomer has polymerized to form a copolymer with the SQAC, the stabilized, partially polymerized microemulsion is then further diluted to 5% or less active SQAC with demineralized water to form a water stable, crystal clear microemulsion with a stable viscosity and clarity for greater than 6 months.

2. The process of claim 1, wherein the SQAC to form stable microemulsions is defined as 3-(trimethoxysilyl) propyl-N-octadecyl-N,N-dimethyl ammonium chloride and their trisilanol, polysiloxanol and water soluble polysiloxane derivatives.

3. The process of claim 1, wherein the essential oil or extract used to form the stable microemulsions is selected from the group consisting of grapefruit, lemon, lime, orange, tangerine, and orange peel.

4. The process of claim 1, wherein a partially polymerized aqueous solution of SQAC is generated by raising the concentration, the pH and/or the temperature to facilitate an increase in the rate of polymerization.

5. The process of claim 1, wherein a partially polymerized aqueous solution of SQAC is stopped or retarded by lowering the concentration by dilution with water, lowering the pH and/or the temperature prior to or after adding the essential oil stabilized microemulsion.

6. The process of claim 1, wherein the chlorosilanol is chloropropyltrimethoxysilane or chloropropyltriethoxysilane.

7. The process of claim 1, wherein the essential oil stabilized SQAC microemulsion contains from 3% to 40% essential oil based on active weight of anhydrous SQAC.

8. The process of claim 1, wherein the amount of essential oil stabilized, partially polymerized microemulsion added to the partially polymerized unstabilized SQAC solution is from 0.001% to 200% of the weight of the partially polymerized unstabilized solution.

9. The process of claim 1, wherein the mixture of the partially polymerized SQAC solution and the essential oil stabilized microemulsion form a water stable mixture that remains crystal clear, without separation, precipitation or further significant viscosity gain.

10. The process of claim 1, wherein the temperature during the partial polymerization process is 10° C. to 100° C.

11. A process of claim 10 where the temperature during the partial polymerization process is 25° C. to 35° C.

12. The process of claim 1, wherein the pH of the SQAC solution during the partial polymerization is pH 2 to pH 8 and the pH is adjusted with solutions of hydrochloric acid or sodium hydroxide.

13. A process of claim 12 where the pH of the SQAC solution during the partial polymerization is between pH 3 to pH 7 and the pH is adjusted with solutions of hydrochloric acid or sodium hydroxide.

14. The process of claim 1, wherein the resultant essential oil stabilized, partially polymerized, crystal clear SQAC microemulsion is diluted to 0.01% to 5.0% active SQAC, and used to treat building and construction materials, textiles and manufactured items to provide a durable, non-leaching chemically bonded antimicrobial barrier on the substrate treated.

15. The process of claim 1, wherein the resultant stabilized, partially polymerized SQAC microemulsion is used as an additive to shampoos, liquid soaps and hand sanitizers, both foaming and gel, to treat animal and human hair, nails and skin, providing a durable, chemically bonded, antimicrobial barrier that lasts through many washes and provides up to 3 days of reduction or elimination of bacteria, viruses and fungi.

16. The process of claim 1, wherein the resultant stabilized, partially polymerized microemulsion is added to benzalkonium chloride based hand sanitizers and soaps without causing a noticeable increase in solution turbidity and provides a durable chemically bonded antimicrobial barrier without interfering with the benefits of the benzalkonium chloride based hand sanitizer and soap design or its ability to foam.

* * * * *